(12) United States Patent
Benham (10) Patent No.: US 6,966,328 B2
(45) Date of Patent: Nov. 22, 2005

(54) FLUID DIVERSION APPARATUS

(76) Inventor: Roger A. Benham, P.O. Box 120830, San Diego, CA (US) 92112-0830

( * ) Notice: Subject to any disclaimer, the term of this patent is extended or adjusted under 35 U.S.C. 154(b) by 120 days.

(21) Appl. No.: 10/270,104

(22) Filed: Oct. 15, 2002

(65) Prior Publication Data

US 2003/0070718 A1    Apr. 17, 2003

Related U.S. Application Data

(60) Provisional application No. 60/329,324, filed on Oct. 16, 2001.

(51) Int. Cl.$^7$ ............................................ G05D 111/03
(52) U.S. Cl. .......................... 137/101.11; 137/315.01; 137/599.12
(58) Field of Search ................... 137/101.11, 205.5, 137/268, 599.11, 599.12, 599.14, 599.121, 137/315.01

(56) References Cited

U.S. PATENT DOCUMENTS

| | | | |
|---|---|---|---|
| 3,021,862 A | * | 2/1962 | Miller ..................... 137/205.5 |
| 3,776,274 A | | 12/1973 | Riley ....................... 137/205.5 |
| 3,974,847 A | * | 8/1976 | Hodges .................. 137/101.11 |

* cited by examiner

Primary Examiner—Stephen M. Hepperle
(74) Attorney, Agent, or Firm—Jean A. Buttmi; Hoffman Wasson & Gitler PC (57) ABSTRACT

A fluid diversion apparatus, which has a first member and a second member, each said member having at least one fluid inlet and at least one fluid outlet, the first member comprising a fluid inlet adapted for connection to a fluid pipe, and a fluid outlet adapted for connection to a fluid pipe such that fluid passing through the fluid pipes passes through the first member in a fluid flow direction, and a connecting means, the second member being attached to the first member via the connecting means, the second member having a first end and a second end, the first end being positioned inside the first member, the first end having an inlet means and an outlet means, the second end of the second member having an inlet and an outlet, the inlet of the first end of the second member is in fluid connection with the outlet of the second end and the outlet of the first end is in fluid connection with the inlet of the second end.

19 Claims, 5 Drawing Sheets

FLUID DIVERSION APPARATUS

The present application is based upon U.S. provisional patent application Ser. No. 60/329,324, filed Oct. 16, 2001.

BACKGROUND OF THE INVENTION

1. Field of the Invention

The present invention relates to a fluid diversion apparatus and in particular to an apparatus wherein a single fitting allowing a portion of the fluid to be diverted, manipulated and then reintroduced, is attached to the main fluid flow line.

2. Background Art

Methods and apparatus for dispensing treatment products into a liquid stream are known. These methods usually involve the use of power-driven or electrical metering pumps. These pumps apply a force to the additive and through this, move the additive into the liquid stream. The dispersal is left to the inherent vortices and eddies in the fluid stream.

Also the "bypass" type fluid diversion apparatus is known. These are generally associated with chemical feeders or dispensers. In this type of known diversion apparatus, the system comprises a main flow stream pipe in which the fluid to be treated flows in one determined direction. For the purposes of introducing fresh untreated liquid to the chemical dispenser, the dispenser is fitted with an inlet port. For the purpose of providing outflow, the chemical dispenser is fitted with an outlet port. The inlet port is connected by a suitable conduit to the upstream side of the pipe. In a like manner, the outlet port is connected to the downstream side of the pipe by means of a conduit.

In order to provide optimum flow control and thereby control the amount of chemical added to the liquid stream, a pair of valves are generally provided, one on each conduit. These valves provide a means for stopping flow through the dispenser for servicing and addition of chemical product. They also are generally sensitive, to provide an accurate control over both the flow of fresh liquid into the dispenser and the quantity of solution being drawn from the dispenser and added to the flow stream.

In order to provide for adequate flow of liquid through the dispenser in the direction desired, a restriction is provided in the main line between the inlet conduit and the outlet conduit which creates a pressure differential across the inlet and outlet of the dispenser so as to direct the flow as desired. Generally, a venturi is provided, converging in a direction towards the outlet conduit and having a throat of sufficient restriction to provide a pressure differential which is adequate to permit the required flow to be attained through the chemical dispenser.

In a second known configuration, the restriction is a throttling valve placed on the main flow stream pipe, between the inlet conduit and outlet conduit valves. By closing the valve, a pressure differential is created across the inlet and outlet of the dispenser so as to direct the flow as desired.

In a third known configuration, a dip tube type of bypass diverter is used, wherein a tube having an entry hole is placed in the main flow stream line, perpendicular to the direction of flow. This entry hole allows for a scooping up of liquid, which then proceeds to the dispenser and is sucked back into the main flow at a second downstream tube also perpendicular to the direction of the main flow stream. The second tube, which returns the fluid to the main flow stream, typically has an angled tip, with the angled portion facing away from the direction of flow.

In the above configurations, the apparatus requires the use of two conduits (generally tee-fittings), and this is disadvantageous when an installation is required in a tight area lacking access. Alternative bypass arrangements require other fittings or adaptations be made to the main stream pipe and so hamper the construction of the apparatus. The throttling valve and venturi rely on the pressure created to drive the bypass liquid through the dispenser, not ram type pressure of the liquid due to its velocity in the main stream pipe.

The bypass-type fluid diversion apparatus provides a useful alternative to using metering pumps, which can be expensive and also require maintenance. The fluid diversion apparatus as described here can also be replaced in the event of problems, far more easily than a valve or venturi which will be generally securely attached to the main flow stream pipe usually by welding or brazing. It is also less often in need of maintenance due to the use of corrosion resistant materials in manufacture.

BRIEF SUMMARY OF THE DISCLOSURE

The present invention is directed to a fluid diversion apparatus, which may at least partially overcome the above-mentioned disadvantages or provide the consumer with a useful and commercial choice.

In one form, the invention resides in a fluid diversion apparatus, which has a first member and a second member, each said member having at least one fluid inlet and at least one fluid outlet, the first member comprising a fluid inlet adapted for connection to a fluid pipe, and a fluid outlet adapted for connection to a fluid pipe such that fluid passing through the fluid pipes passes through the first member, and a connecting means, the second member being attached to the first member via the connecting means, the second member having a first end and a second end, the first end being positioned inside the first member, the first end having an inlet means and an outlet means, the second end of the second member having an inlet and an outlet, the inlet of the first end of the second member is in fluid connection with the outlet of the second end and the outlet of the first end is in fluid connection with the inlet of the second end.

The fluid diversion apparatus as described herein shall preferably be used as a part of a bypass type chemical dispensing system comprising a main flow stream pipe in which the fluid to be treated flows in one determined direction. For the purposes of introducing fresh untreated liquid to the chemical dispenser, the dispenser generally has an inlet port and for the purpose of providing outflow, the chemical dispenser is fitted with an outlet port. The inlet port is connected by a suitable conduit to the upstream side of the pipe. In a like manner, the outlet port is connected to the downstream side of the pipe by means of a conduit.

The first member may preferably be a "T"-shaped fitting with an internally threaded tubular extension shank or an elbow fitting with a tubular extension from the point of the elbow having an internally threaded section. The cross-piece may preferably be fitted parallel to the direction of fluid flow in the fluid pipes and the tubular extension shank allows diversion of a portion of the fluid in another direction. The first member may be fitted to the main stream pipe of a bypass type chemical dispensing system Preferably, the first end of the second member will be formed of two concentric, coaxial tubes. A molded lip may be provided on the first end of the inner tubular member to help prevent the inner tube from being ejected due to the pressure caused by operation at maximum flow rates. The outer tube will have an opening facing the direction of flow and this will be the inlet means for the fluid. The inner tube will form the outlet for the fluid and will be spaced coaxially from the outer tube and is permanently separated from the outer tube along its length until the second end where the space shall be sealed by appropriate sealing means. This sealing means may preferably take the form of a rubber packing seal.

The second member may preferably be manufactured as a substantially unitary member.

In a particularly preferred embodiment, the second member may preferably be manufactured as a number of individual parts to be assembled to form the second member.

The individual parts of the second member may preferably comprise an inner tube, an outer tube and a body portion, having three threaded openings. The openings may be a first opening allowing attachment of the outer tube to the body portion, a second opening forming the outlet at the second end of the second member and a third opening to engage with the inner tube at the inlet at the second end of the second member.

The provision of a number of individual parts, each of which is attachable to each other, allows the second member to be dismantled for servicing and cleaning and also replacement of parts. It may also preferably allow the rotation of individual parts in relation to one another to allow adjustment of the apparatus.

The first opening of the body portion may be a lower, internally-threaded opening. The internally threaded opening may engage with an externally threaded bushing. This bushing may suitably be permanently attached to the outer tube. This configuration may allow the removal of the outer tube from the body portion without disruption of the inner tube.

The second opening of the body portion may suitably be an externally threaded opening. This opening may be engageable with a control or stop valve having an internally threaded portion.

The third opening may also suitably be an externally threaded opening with a substantially smooth interior. This opening may be engageable with a control or stop valve.

The interior of the third opening may suitably engage the inner tube. This engagement may be a loose fit or interference fit. In either situation, a rubber packing seal may be used to form or enhance a fluid tight seal. The inner tube may preferably extend through the third opening and through the body portion extending out of the first opening of the body portion.

A loose fit between the body portion and the inner tube may preferably allow the rotation of each of the components with respect to the other components or the first member.

This configuration may allow the removal and/or replacement of the inner tube without disruption or removal of the outer tube or removal of the second member from the first member.

All of the threaded openings may be engageable with a threaded member or bushing to interconnect the portions in a substantially fluid tight manner. In all cases, additional seals may be provided.

The three openings in the body portion may suitably all be in fluid connection with each other when the body portion is manufactured. The flow pattern through the fluid diversion apparatus is achieved when the second member is in it's assembled from.

The assembly of the second member from its component parts may suitably follow the pattern of inserting the inner tube into the third opening in the body portion and forming a fluid tight seal thereabout. The outer tube may then be attached to the first opening by positioning it coaxially about the inner tube and securing the threaded bushing attached to the outer tube, to the body portion. The first and second openings of the body portion may then be secured to the control or stop valves.

The control or stop valves may allow the placement of the fluid diversion apparatus in a chemical dispensing system.

The connecting means for connecting the second member to the first member will preferably be in the form of a connection bushing, brazed to the outside of the second member. The connecting means will form a substantially fluid impervious seal between the first and second members. The connection bushing will have an external threaded section to be engagedly received by a corresponding internally threaded section on the interior of the hollow, tubular extension of the first member. This will preferably eliminate the need for a rubber packing seal and a packing nut although these may be used, resulting in a more reliable, leak-free means of installation.

Preferably, the inlet and outlet at the second end of the second member will each be attached to a flow controlling or stopping device, such as a control or stop valve.

Both the inner and outer tube shall preferably have, at the first end of the second member, a bevelled plane terminus. The bevelled plane shall preferably face away from the direction of flow in the main flow stream. The inlet tube preferably will extend the further than the plane terminus of the outer tubular member, creating a pressure differential to divert a portion of the liquid from the fluid pipe of the main flow stream into the fluid diversion apparatus and the bypass flow stream.

The inner tube of the second member shall also preferably be manufactured using a corrosion resistant or non-metallic material.

In a broad form, the invention resides in a fluid diversion apparatus comprising a fluid inlet to the fluid diversion apparatus and a fluid outlet from the fluid diversion apparatus fitted as a single fitting to a main fluid flow pipe in a bypass type chemical dispenser system.

In another broad form, the invention resides in a fluid diversion apparatus, which has a first member and a second member, each said member having at least one fluid inlet and at least one fluid outlet, the first member comprising a fluid inlet adapted for connection to a main fluid pipe of a bypass-type dispenser system, and a fluid outlet adapted for connection to a main fluid pipe of a bypass-type dispenser system such that fluid passing through the main fluid pipe passes through the first member in a fluid flow direction with at least a portion of the fluid passing through the second member, and a connecting means, the second member being attached to the first member via the connecting means.

BRIEF DESCRIPTION OF THE DRAWINGS

A number of embodiments of the invention will be described with reference to the following drawings, in which.

While the invention hereinafter disclosed is susceptible of various modifications and alternative constructions, particular illustrative embodiments have been shown in the drawing and will hereinafter be described in detail. It will be understood that there is no intention to limit the invention to the specific form disclosed but, on the contrary, the invention is to cover all modifications, alternative constructions and equivalents falling within the spirit and scope of the invention.

DETAILED DESCRIPTION

According to one aspect of the present invention, a fluid diversion apparatus is provided.

The fluid diversion apparatus comprises a first member 10 having a fluid inlet for connection 11 to a fluid pipe. It also possesses a fluid outlet for connection 12 to a fluid pipe. The first member inlet means 11 and outlet means 12 shall be of suitable size and shape to be fitted to a main flow stream pipe 13. Due to the design of most modern plumbing systems, the main flow stream pipe 13 will generally be circular although some fluid systems use non-circular pipes.

The first member 10 also has a connecting means 14 interposed between the inlet 11 and the outlet 12. This connecting means will also generally be circular and shall terminate in a threaded section 15.

According to a preferred embodiment of the invention the first member will be a "T-shaped" member for use in a straight pipe.

Figure 3:
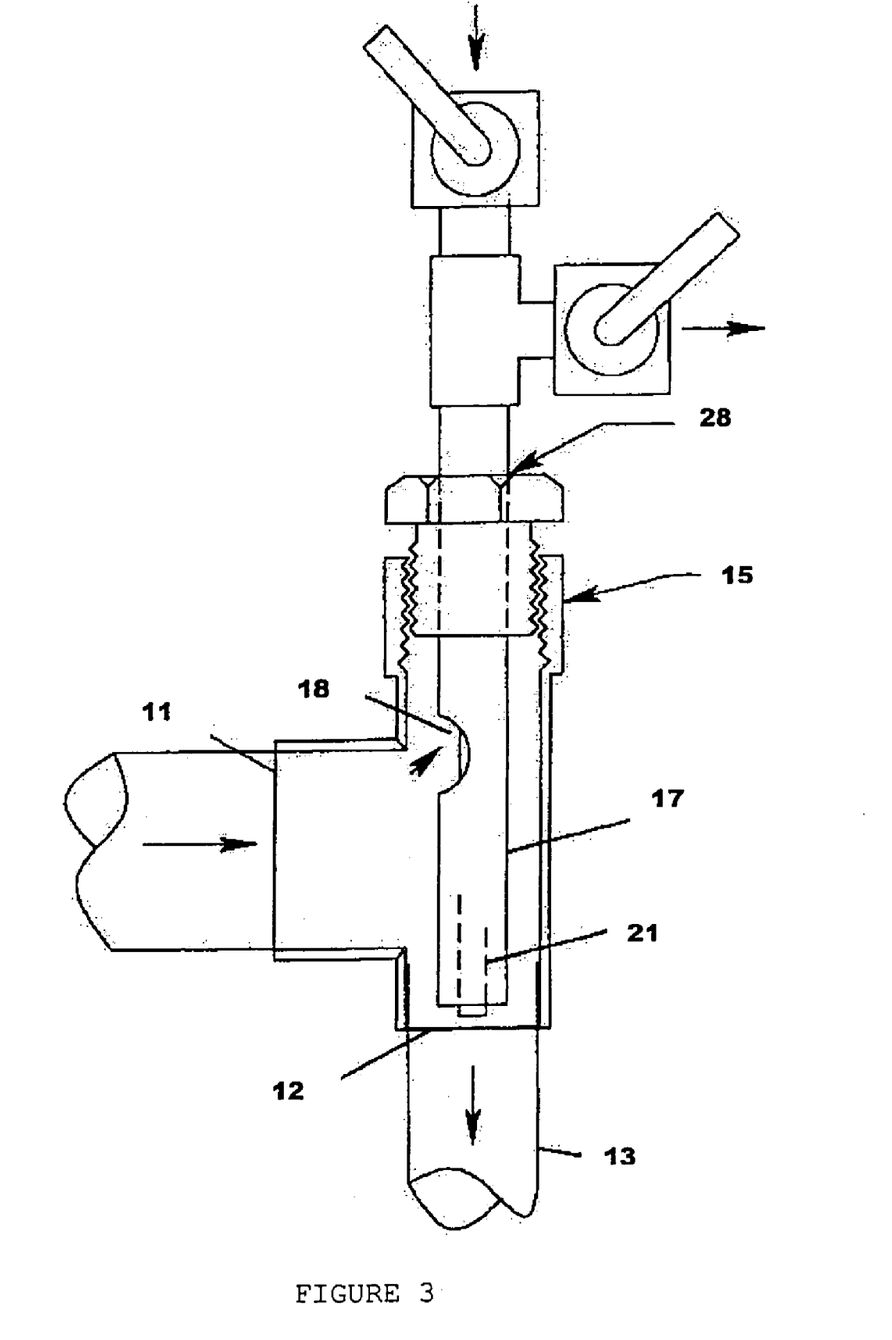
FIG. 3 is an elevation view of a second preferred embodiment of the apparatus showing detail of the first and second members and their preferred connection means as connected in an elbow installation.

According to a second preferred embodiment of the invention, as shown in FIG. 3, the first member 10 will be an elbow member for installation in an angled situation.

The fluid diversion apparatus also comprises a second member 16. The second member 16 also possesses a first end and a second end.

The first end of the second member 16 comprises two coaxial tubular members.

The outer tubular member 17 has an inlet end 23 and an outlet end 22. The outer tubular member 17 has a fluid entry hole 18 positioned adjacent to the extremity of the member at the inlet end of the outer tubular member 19. This fluid entry hole 18 will be large enough to divert some of the fluid from the main flow stream fluid 13 into the outer tubular member 17. The outer tubular member 17 of the second member, when connected to the first member 10, will extend substantially into the main flow stream fluid allowing the correct positioning of the fluid entry hole 18. According to the first preferred embodiment as shown in FIG. 1, the end of the outer tubular member 17 adjacent to the fluid entry hole 18 will terminate in a bevelled plane 20 of approximately 45-degree slope facing away from the direction of flow in the main flow stream.

Figure 1:
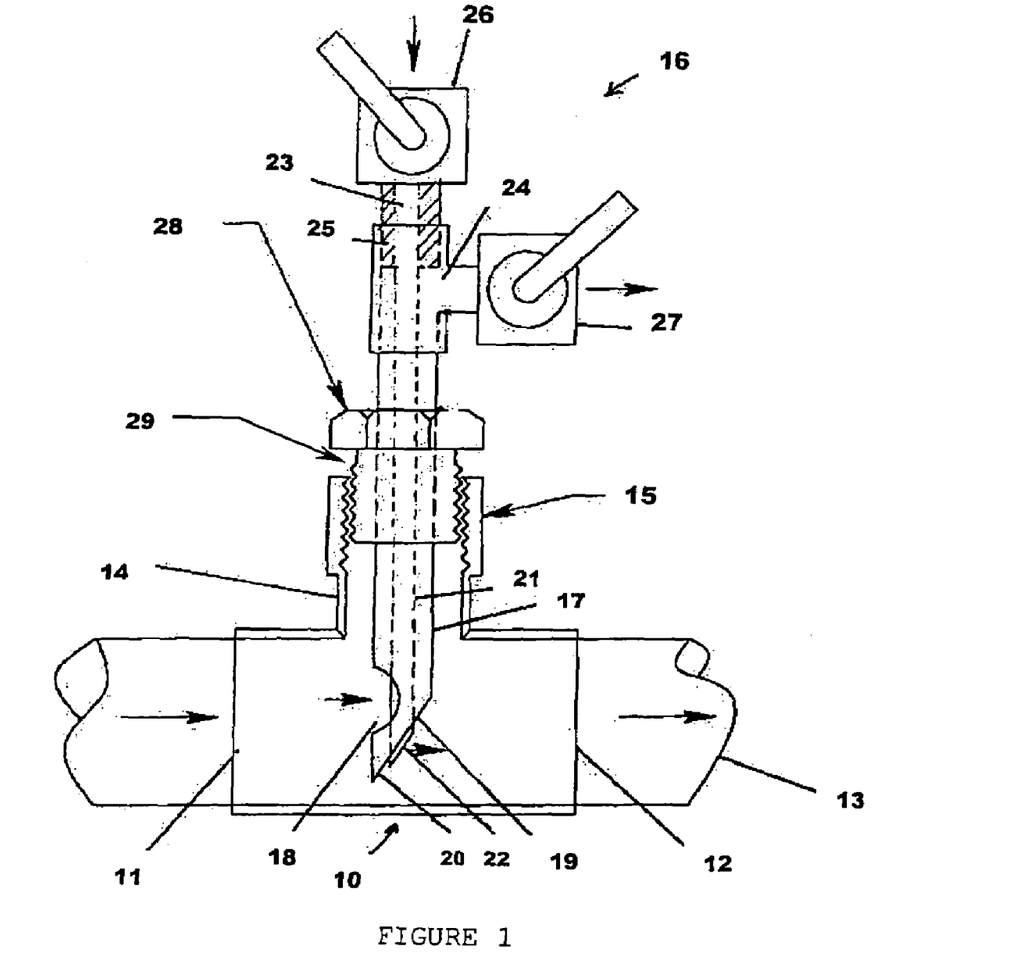
FIG. 1 is an elevation view of the apparatus showing detail of the first and second members and their preferred connection means in a simple pipe installation.
Figure 2:
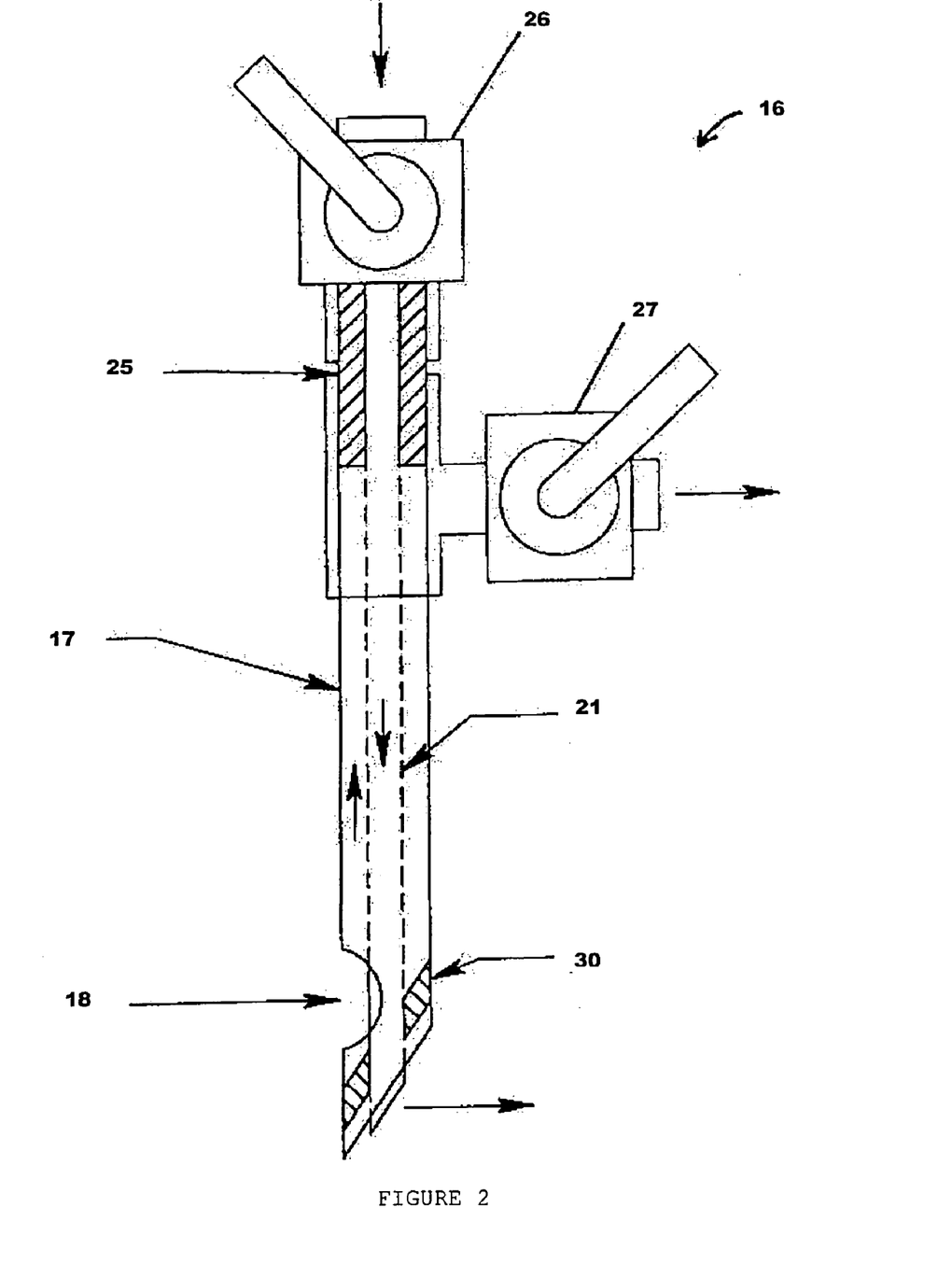
FIG. 2 is an elevation view of the second member showing detail of the direction of liquid flow.

According to the first preferred embodiment as shown in FIGS. 1 and 2, the inner tubular member 21 will be smaller in diameter than the outer tubular member 17. The inner tubular member will terminate also in a bevelled plane 20 of approximately 45-degree slope facing away from the direction of flow in the main flow stream. This terminus will be at the outlet end of the inner tubular member 22. The outlet end of the inner tubular member 22 will be aligned with the inlet end of the outer tubular member 19, but shall extend further into the main flow stream. The inner tubular member 22 and the outer tubular member 17 will be separated at the first end of the second member 16 by a lower sealing bushing 30. This bushing may be manufactured of any fluid impermeable material and is so placed to prevent the fluid flowing in the fluid entry hole 18 and exiting out of the lower extremity of the outer tubular member 19.

Figure 5:
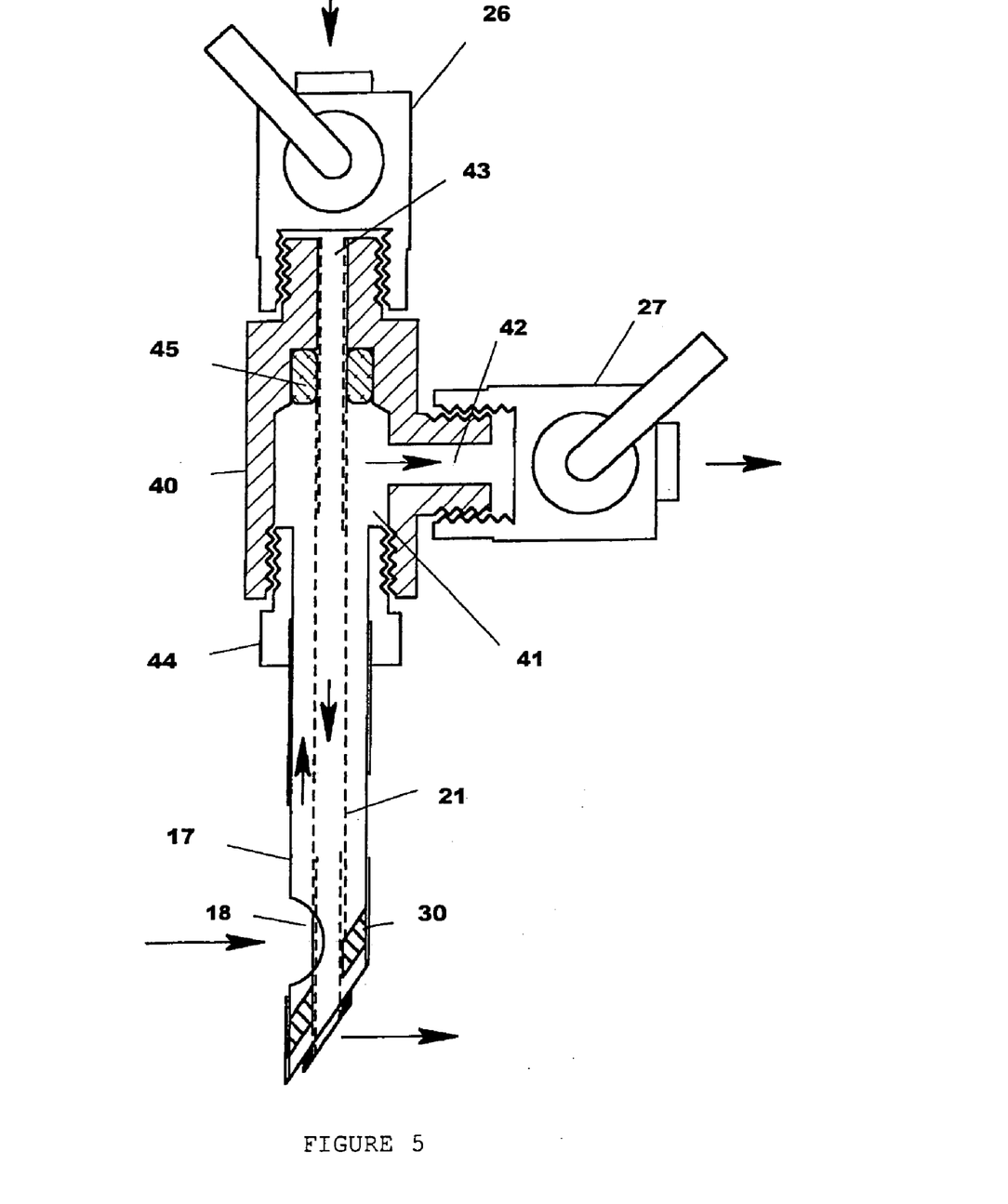
FIG. 5 is an elevation view of preferred aspect of the second member showing detail of the direction of liquid flow and T-shaped fitting with a sealing means at the second end of the inner tube.

The outlet end of the inner tubular member 22 will be in fluid connection with the inlet end of the inner tubular member 23, at the second end of the second member 16. This inlet end of the inner tubular member 23 shall be surrounded by an upper sealing bushing 25, which will be positioned contiguously to both the inner tubular member 21 and the outer tubular member 17. The purpose of the upper sealing bushing 25 is to separate the inner tubular member 21 and the outer tubular member 17. A permanent contiguous seal can be accomplished with a rubber packing bushing (FIG. 5). This feature allows the removal of the second end of the second member at the threaded fitting. The threaded fitting allows a swivelling motion about the axis of the inner tube allowing the direction of the outlet valve to be adjusted in the field by simply rotating about the threaded joint.

The inlet end of the outer tubular member 19 will be in fluid connection with the outlet end of the outer tubular member 24 at the second end of the second member 16. The fluid connection shall take the form of a "T"-shaped fitting surrounding the outer tubular member 17.

At the second end of the second member 16, both the inlet and outlet shall be connected to an inlet valve 26 and an outlet valve 27 respectively. These valves will be a flow controlling or stopping device, such as a control or stop valve. They will be connected in such a way as to provide the apparatus with a means to control the velocity with which the fluid enters and leaves the diversion area.

In the preferred embodiment shown in FIG. 5, the second member 16 is manufactured as a number of individual parts to be assembled to form the second member 16.

The individual parts of the second member 16 comprise an inner tube 21, an outer tube 17 and a body portion 40, having three threaded openings. The openings are a first opening 41, allowing attachment of the outer tube 17 to the body portion 40, a second opening 42 forming the outlet at the second end of the second member 16 and a third opening 43 to engage with the inner tube 21 at the inlet at the second end of the second member 16.

The first opening 41 of the body portion 40 is a lower, internally-threaded opening. The first opening 41 engages with an externally threaded bushing 44. This bushing 44 is permanently attached to the outer tube 17. This configuration allows the removal of the outer tube 17 from the body portion 40 without disruption of the inner tube 21.

The second opening 42 of the body portion 40 is an externally threaded opening. This second opening 42 is engageable with a control or stop valve 27 having an internally threaded portion.

The third opening 43 is also suitably an externally threaded opening with a substantially smooth interior. This opening 43 is engageable with a control or stop valve 26.

The interior of the third opening engages the inner tube 21. This engagement is a loose fit. A rubber packing seal 45 is used to form or enhance a fluid tight seal. The inner tube 21 extends through the third opening 43 and through the body portion 40 extending out of the first opening 41 of the body portion 40.

This configuration allows the removal and/or replacement of the inner tube 21 without disruption or removal of the outer tube 17 or removal of the second member 16 from the first member 10.

All of the threaded openings are engageable with a threaded member or bushing to interconnect the portions in a substantially fluid tight manner. In all cases, additional seals may be provided.

The connecting means for connecting the second member will preferably be in the form of a connection bushing 28, brazed to the outside of the second member 16. This connection bushing will be preferably shaped as a hexagonal nut to facilitate its adjustment with standard plumbing or multi-purpose tools. The connecting means will form a substantially fluid impervious seal between the first and second members. The connection bushing 28 will have an external threaded section 29 to be engagedly received by a corresponding internally threaded section 15 on the interior of the connecting means 14 of the first member 10. This will eliminate the need for a rubber seal and packing nut, resulting in a more reliable, leak-free means of installation.

The first member 10 and the second member 16 will both be manufactured of suitable materials for fluid flow fittings. They shall be connected to the main flow stream pipe 13 in a manner which forms a substantially fluid impermeable seal with the main flow stream pipe 13. They will be of suitable proportions to matingly connect with the main flow stream pipe 13 and so will vary in size.

The proportions of the second member 16 will be such that it can be connected to the first member 10.

According to the second preferred embodiment a shown in FIG. 3, the inner tubular member 21 will be smaller in diameter than the outer tubular member 17. The inner tubular member and the outer tubular member will both terminate in a plane parallel with the inlet flow direction. This terminus will be at the outlet end of the inner tubular member 22. The outlet end of the inner tubular member 22 will be aligned with the inlet end of the outer tubular member 19, but shall extend further into the main flow stream. The inner tubular member 22 and the outer tubular member 17 will be separated at the first end of the second member 16 by a lower sealing bushing 30. This bushing may be manufactured of any fluid impermeable material and is so placed to prevent the fluid flowing in the fluid entry hole 18 and exiting out of the lower extremity of the outer tubular member 19.

Figure 4:
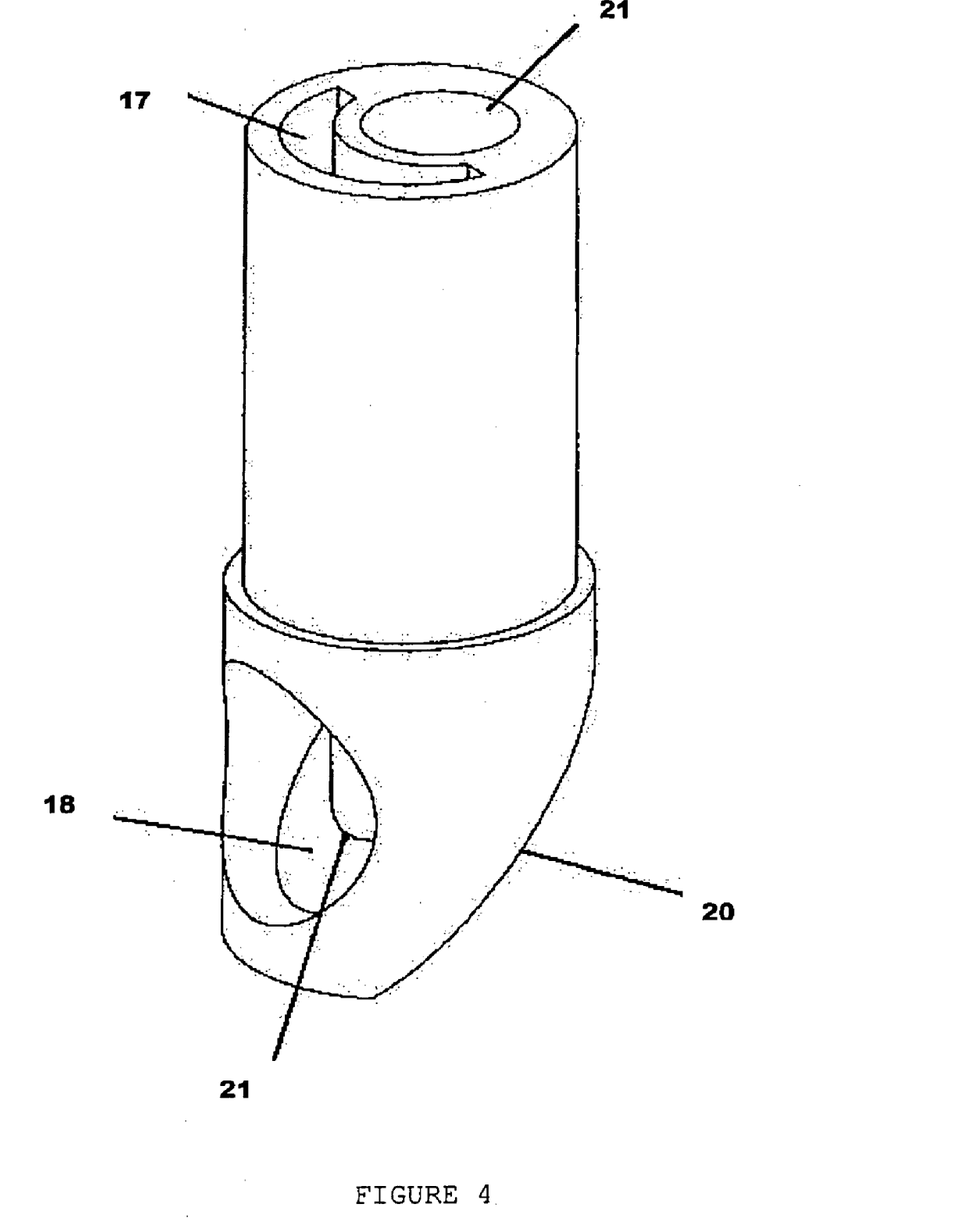
FIG. 4 is an elevation view of a third preferred embodiment of the invention showing a molded insert for replacing the first end of the second member.

According to the third preferred embodiment of the invention, there is provided an insert for replacing the first end of the second member.

The first end of the second member comprises two coaxial tubular members.

The outer tubular member 17 will terminate at a plane parallel to the flow direction in the main flow stream pipe 13. The inner tubular member will also terminate at a plane parallel to the flow direction in the main flow stream pipe 13, but the terminus of the inner tubular member 21 shall be spaced from the terminus of the outer tubular member (17), in a direction perpendicular to the direction of flow in the main flow stream pipe 13. The insert has an inlet end 23 and an outlet end 22. The outer tubular member 17 has a fluid entry hole 18 positioned adjacent to the extremity of the member at the inlet end of the outer tubular member 19. This fluid entry hole 18 will be large enough to divert some of the fluid from the main flow stream fluid into the outer tubular member 17. The outer tubular member 17 of the second member, when connected to the first member 10, will extend substantially into the main flow stream fluid allowing the correct positioning of the fluid entry hole 18.

The fluid diversion apparatus as described herein shall preferably be used as a part of a chemical dispensing system comprising a main flow stream pipe in which the fluid to be treated flows in one determined direction. For the purposes of introducing fresh untreated fluid to the chemical dispenser, the dispenser has an inlet port and an outlet port. The inlet port is in fluid connection, by a suitable conduit, with the outlet of the second end of the second member. In a like manner, the outlet port of the dispenser is in fluid connection with the inlet means of the second end of the second member by means of a conduit.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the description and claims appropriately interpreted by those skilled in the art.

What is claimed is:

1. A fluid diversion apparatus, which has a first member and a second member, each said member having at least one fluid inlet and at least one fluid outlet, the first member comprising a fluid inlet adapted for connection to a fluid pipe, and a fluid outlet adapted for connection to a fluid pipe such that fluid passing through the fluid pipes passes through the first member in a fluid flow direction, and a connecting means, the second member being attached to the first member via the connecting means, the second member having a first end and a second end, the first end being positioned inside the first member, the first end having an inlet means and an outlet means, the first end of the second member being formed of two concentric, coaxial tubular members, an inner tubular member and an outer tubular member, the second end of the second member having an inlet and an outlet, the inlet of the first end of the second member being in fluid connection with the outlet of the second end and the outlet of the first end being in fluid connection with the inlet of the second end.

2. The fluid diversion apparatus as claimed in claim 1 wherein the first member is a "T"-shaped fitting, the cross-piece of the fitting positioned parallel to the direction of fluid flow in the fluid pipe and a threaded tubular extension allowing diversion of a portion of the fluid in another direction and attachment of the second member.

3. The fluid diversion apparatus as claimed in claim 1 wherein the first member is an elbow fitting with a tubular extension from the point of the elbow having an internally threaded section for attachment of the second member.

4. The fluid diversion apparatus as claimed in claim 1 wherein the first member is fitted to a main stream pipe of a bypass type chemical dispensing system.

5. The fluid diversion apparatus as claimed in claim 1 wherein the outer tubular member has an opening facing the direction of flow, being the inlet means for the fluid and the inner tubular member is the outlet for the fluid and is permanently seperated from the outer tubular member along its length until the second end where the space is sealed by appropriate sealing means.

6. The fluid diversion apparatus as claimed in claim 1 wherein the second member is manufactured as a number of individual parts to be assembled to form the second member.

7. The fluid diversion apparatus as claimed in claim 6 wherein the individual parts forming the second member comprise the inner tubular member, the outer tubular member and a body portion, said body portion having three openings, a first opening allowing attachment of the outer tubular member to the body portion, a second opening forming the outlet at the second end of the second member and a third opening to engage with the inner tubular member at the inlet at the second end of the second member.

8. The fluid diversion apparatus as claimed in claim 7 wherein the first opening of the body portion comprises a lower, internally-threaded opening to engage with an externally threaded bushing permanently attach to the outer tubular member.

9. The fluid diversion apparatus as claimed in claim 7 wherein the second opening of the body portion comprises an externally threaded opening engageable with a control or stop valve having an internally theaded portion.

10. The fluid diversion apparatus as claimed in claim 7 wherein the third opening comprises an externally threaded opening with a substantially smooth interior, the interior of the third opening engaging the inner tubular member, the inner tubular member extending through the third opening and through the body portion and extending out of the first opening of the body portion.

11. The fluid diversion apparatus as claimed in claim 6 wherein all of the individual parts forming the second member are engageable in a threaded manner to interconnect the parts in a substantially fluid tight manner.

12. The fluid diversion apparatus as claimed in claim 7 wherein the assembly of the second member from its component parts follows the pattern of inserting the inner tubular member into the third opening in the body portion and forming a fluid tight seal, attaching the outer tubular member to the first opening by positioning it coaxially about the inner tube and securing the outer tubular member to the body portion, securing the first and second openings of the body portion to the control or stop valves.

13. The fluid diversion apparatus as claimed in claim 1 wherein control or stop valves are provided allowing the placement of the fluid diversion apparatus in a chemical dispensing system.

14. The fluid diversion apparatus as claimed in claim 1 wherein the connecting means for connecting the second member to the first member is a connection bushing, brazed to the outside of the second member, the connecting means having an external threaded section to be engagedly received by the threaded tubular extension of the first member.

15. The fluid diversion apparatus as claimed in claim 2 wherein the connecting means for connecting the second member to the first member is a connection bushing, brazed to the outside of the second member, the connecting means having an external threaded section to be engagedly received by the threaded tubular extension of the first member.

16. The fluid diversion apparatus as claimed in claim 1 wherein both the inner and outer tubular members have, at the first end of the second member, a bevelled plane terminus, the bevelled plane facing away from the fluid flow direction, the inner tubular member extending further than the plane terminus of the outer tubular member, creating a pressure differential to divert a portion of the liquid from the fluid pipe into the fluid diversion apparatus.

17. The fluid diversion apparatus as claimed in claim 16 wherein the first end of the second member comprises a molded insert having a tubular body with a first passage having a first end and a second end, the first end of the first passage for engaging with the inner tubular member and a second passage having a first end and a second end, the first end of the second passage for engaging with the outer tubular member, the second end of the first passage extending further than a plane of the second end of the second passage, creating a pressure differential to divert a portion of the liquid from the fluid pipe into the fluid diversion apparatus.

18. A fluid diversion apparatus as claimed in claim 1 comprising a fluid inlet to the fluid diversion apparatus and a fluid outlet from the fluid diversion apparatus fitted as a single fitting to a main fluid flow pipe in a bypass type chemical dispenser system.

19. A fluid diversion apparatus, which has a first member and a second member, each said member having at least one fluid inlet and at least one fluid outlet, the first member comprising a fluid inlet adapted for connection to a main fluid pipe of a bypass-type dispenser system, and a fluid outlet adapted for connection to a main fluid pipe of a bypass-type dispenser system so that fluid passing through the main fluid pipe passes through the first member in a fluid flow direction with at least a portion of the fluid passing through the second member, and a connecting means, the second member being attached to the first member via the connecting means, the second member having a first end and a second end, the first end being positioned inside the first member, the first end having an inlet means and an outlet means, the first end of the second member being formed of two concentric, coaxial tubular members, an inner tubular member and an outer tubular member, the second end of the second member having an inlet and an outlet, the inlet of the first end of the second member being in fluid connection with the outlet of the second end and the outlet of the first end being in fluid connection with the inlet of the second end.

* * * * *